United States Patent

Wei et al.

[11] Patent Number: 6,053,613
[45] Date of Patent: Apr. 25, 2000

[54] OPTICAL COHERENCE TOMOGRAPHY WITH NEW INTERFEROMETER

[75] Inventors: Jay Wei, Fremont, Calif.; David Huang, Atlanta, Ga.; Christopher L. Petersen, Danville, Calif.

[73] Assignee: Carl Zeiss, Inc., Thornwood, N.Y.

[21] Appl. No.: 09/079,908

[22] Filed: May 15, 1998

[51] Int. Cl.$^7$ ............................................ A61B 3/10
[52] U.S. Cl. .................................. 351/205; 382/103
[58] Field of Search ............................. 382/103; 356/345, 356/357, 358, 360; 351/205, 206, 212; 606/4, 10

[56] References Cited

U.S. PATENT DOCUMENTS

| 5,321,501 | 6/1994 | Swanson et al. | 356/345 |
|---|---|---|---|
| 5,491,524 | 2/1996 | Hullmuth et al. | 351/212 |
| 5,644,642 | 7/1997 | Kirschbaum | 382/103 |
| 5,847,827 | 12/1998 | Frecher | 356/345 |
| 5,892,583 | 4/1999 | Li | 356/345 |

FOREIGN PATENT DOCUMENTS

| 9219930 | 11/1992 | WIPO | G01B 9/02 |
|---|---|---|---|
| WO97/32182 | 9/1997 | WIPO | G10B 11/12 |

OTHER PUBLICATIONS

Optical Measurement of the Axial Eye Length by Laser Doppler Interferometry, C. K. Hitzenberger, Invest Ophth. & Vis. Sci., vol. 32, No. 3, mar. 1991, pp. 616–624.

Polarization–Independent Interferometric Optical–Time-–Domain Reflectometer, M. Kobayashi et al., *J. of Lightwave Tech.*, vol. 9, No. 5, May 1991, pp. 623–628.

Optical Fiber Component Characterization by High–Intensity and High–Spatial–Resolution Interferometric Optical-–Time Domain Reflectometer, M. Kobayashi et al., *IEEE Phot. Tech. Letters*, vol. 3, No. 6, Jun. 1991, pp. 564–566.

Rayleigh backscattering measurement of single–mode fibers by low coherence optical time–domain reflectometer with 14 $\mu$m spatial resolution, K. Takada et al., *Appl. Phys. Lett.*, vol. 59, No. 2, Jul. 8, 1991, pp. 143–145.

Resolution Control of Low–Coherence Optical Time–Domain Reflectomer Between 14 290 $\mu$m, K. Takada et al., *IEEE Phot. Tech. Lett.*, vol. 3, No. 7, Jul. 1991, pp. 676–678.

Phase–noise and shot–noise limited operations of low coherence optical time domain reflectometry, K. Takada et al., *Apply. Phys. Lett.*, vol. 59, No. 20, nov. 11, 1991, pp. 2483–2485.

Optical Coherence Tomography by Huang et al., *Science*, 254, nov. 22, 1991, pp. 1178–1181.

(List continued on next page.)

*Primary Examiner*—George Manuel
*Attorney, Agent, or Firm*—Michael B. Einschlag

[57] ABSTRACT

Embodiments of the present invention are method and apparatus for simply and economically providing efficient scanning in an optical coherence tomography ("OCT") apparatus. In particular, an embodiment of the present invention is an OCT apparatus which examines an object, which OCT apparatus comprises: (a) a source of short coherence radiation; (b) a coupler which (i) couples a first portion of the radiation to a reference arm; (ii) couples a second portion of the radiation to a sample arm; (iii) combines radiation transmitted thereto from the reference path and the sample path; and (iv) couples the combined radiation to an analyzer; wherein (c) the reference arm transmits the first portion of the radiation to a measurement range variation apparatus and transmits radiation output from the measurement range variation apparatus back to the coupler; (d) the sample path transmits the second portion of the radiation to the object and transmits radiation scattered by the object back to the coupler; and (e) the measurement range variation apparatus comprises: (i) a transmitter which transmits a portion of the radiation incident thereupon; (ii) a reflector which reflects radiation transmitted by the transmitter; and (iii) a scanner coupled to scan the reflector.

27 Claims, 5 Drawing Sheets

OTHER PUBLICATIONS

In vivo retinal imaging by optical coherence tomography by E. A. Swanson, J. A. Izatt, M. R. Hee, D. Huang, C. P. Lin, J. S. Schuman, and C. A. Puliafito, *Optics letters*, vol. 18, No. 21, Nov. 1, 1993, pp. 1864–1866.

Coherent optical tomography of microscopic inhomogeneities in biological tissues, V. M. Gelikonov et al., *JETP Lett.*, vol. 61, No. 2, Jan. 25, 1995, pp. 158–162.

Optical Coherence Tomography, A. F. Fercher, *J. Biomed. Optics*, vol. 1, No. 2, Apr. 1996, pp. 157–173.

OPTICAL COHERENCE TOMOGRAPHY WITH NEW INTERFEROMETER

TECHNICAL FIELD OF THE INVENTION

The present invention relates to optical coherence tomography ("OCT") and, in particular, to method and apparatus for OCT which includes an interferometer that enables high resolution measurement with selective measurement ranges.

BACKGROUND OF THE INVENTION

It is well known in the prior art to incorporate low coherence optical interferometers into various optical coherence tomography ("OCT") apparatus to study scattering media. A basic form of such an OCT apparatus found in the prior art comprises an interferometer that includes a 50/50 beamsplitter, or a 3 dB coupler if the interferometer is embodied using optical fibers. In a typical prior art optical fiber embodiment of the OCT apparatus, a low coherence radiation source and a photodetector are coupled to two input ends of the 3 dB coupler. The beams of radiation transmitted from two output ends of the 3 dB coupler are transmitted to a sample medium to be tested and a reference medium, respectively. The beams from the output ends are: (a) reflected from the sample medium and the reference medium, respectively; (b) combined by the 3 dB coupler; and (c) transmitted to the photodetector. As is well known in the prior art, when the optical pathlength mismatch between radiation reflected from the sample medium and radiation reflected from the reference medium is less than the coherence length of the low coherence radiation source, measurable interference occurs between these the two beams. Then, if the optical pathlength of the radiation reflected from the reference medium is known, when the photodetector senses the interference signals, the optical pathlength of the radiation reflected from the sample medium can be measured to the accuracy of the coherence length of the radiation source.

It is also known in the prior art to utilize OCT methods and apparatus to investigate the eye. In doing so, several types of apparatus have been used to provide a reference medium to facilitate measurement of the optical pathlength of radiation reflected from the reference medium. For example, an OCT apparatus disclosed in an article entitled "Optical Coherence Tomography" by David Huang et al., *Science*, Vol. 254, pp. 1178–1181, Nov. 22, 1991 utilized a mirror to reflect a reference beam back to a photodetector. In the disclosed OCT apparatus, depth information for radiation reflected by the sample medium is acquired on a step-by-step basis by moving the mirror with a stepper motor. The disclosed OCT apparatus has been modified in the art, for example, see U.S. Pat. No. 5,321,501. U.S. Pat. No. 5,321,501 discloses: (a) the use of a retroreflector instead of the mirror to improve the optical alignment stability and (b) the use of a galvanometer instead of the stepper motor to increase the scan speed. The increased scan speed is important because it makes it feasible to obtain tomographical images of living tissue. In this regard, in vivo human eye retinal tomography has been demonstrated in an article entitled "In vivo retinal imaging by optical coherence tomography" by Eric Swanson, et al., *Optics Letters*, Vol. 18, No. 21, pp. 1864–1866, Nov. 1, 1993. A disadvantage of such OCT apparatus is that the depth measurement is limited to about 3 mm to 5 mm for in vivo human eye measurement.

An article entitled "Coherent optical tomography of microscopic inhomogeneities in biological tissues" by V. M. Gelikonov et al., *JETP Lett.*, Vol. 61, No. 2, pp. 158–162, Jan. 25, 1995 disclosed the use of a piezoelectric radial actuator with a fixed mirror in the reference arm of an interferometer to fabricate an OCT apparatus. In this OCT apparatus, the optical pathlength of the reference arm is modulated by applying a signal to the piezoelectric actuator, thereby stretching the optical fiber longitudinally. In this arrangement, although the scan speed can be improved, the scan depth is still limited. Further, stretching an optical fiber to increase the scan depth causes other problems such as birefringence and hysteresis.

In light of the above, there is a need for a method and apparatus for simply and economically providing efficient scanning in an OCT apparatus.

In addition to the above, there is a need to utilize the efficient scanning apparatus to perform eye length measurements. At present, eye length measurements are made by measuring the delay of an ultrasound echo back from the retina. Due to the attenuation of ultrasound energy in the eye, only low frequency ultrasound energy can be used. As a result, the accuracy is typically only about 200 $\mu$m. This accuracy represents a measurement error for refraction of approximately ½ diopter and is considered significant in clinical applications such as cataract surgery. Further, this measurement technique suffers because the method requires contact with the eye (this is not comfortable for a patient).

In light of the above, there is a need in the art for method and apparatus for accurately measuring the length of an eye, preferably in a non-contact mode.

An article entitled "Optical Measurement of the Axial Eye Length by Laser Doppler Interferometry" by C. K. Hitzenberger, *Investigative Ophthalmology & Visual Science*, Vol. 32, No. 3, Mar. 3, 1991, pp. 616–624 discloses the use of dual beam Michelson interferometry to measure the eye length using a low coherence light source. The disadvantage of the disclosed configuration is that a bifocal lens is required to focus the beams on the cornea and the retina separately. If this were not done, the signal strength is too weak for imaging the retina. Embodiments of the present invention provide an alternative interferometer configuration to measure eye length without physically increasing the reference beam scan length. In addition, such embodiments are capable of scanning the retinal image with a good signal to noise ratio.

SUMMARY OF THE INVENTION

Advantageously, embodiments of the present invention are method and apparatus for simply and economically providing efficient scanning in an optical coherence tomography ("OCT") apparatus. In particular, an embodiment of the present invention is an OCT apparatus which examines an object, which OCT apparatus comprises: (a) a source of short coherence radiation; (b) a coupler which (i) couples a first portion of the radiation to a reference arm; (ii) couples a second portion of the radiation to a sample arm; (iii) combines radiation transmitted thereto from the reference path and the sample path; and (iv) couples the combined radiation to an analyzer; wherein (c) the reference arm transmits the first portion of the radiation to a measurement range variation apparatus and transmits radiation output from the measurement range variation apparatus back to the coupler; (d) the sample path transmits the second portion of the radiation to the object and transmits radiation scattered by the object back to the coupler; and (e) the measurement range variation apparatus comprises: (i) a transmitter which transmits a portion of the radiation incident thereupon; (ii) a reflector which reflects radiation transmitted by the transmitter; and (iii) a scanner coupled to scan the reflector.

In addition, further embodiments of the present invention are method and apparatus for accurately measuring the length of an eye, preferably in a non-contact mode. Specifically, an embodiment of the present invention is an OCT apparatus as described above which measures a distance between a first and a second scattering portion in the object wherein: (a) the measurement range variation apparatus further comprises a translator coupled to translate the transmitter; and (b) the analyzer comprises: (i) a photodetector which detects radiation coupled from the coupler; (ii) a first filter coupled to output from the photodetector and having a passband centered substantially at a frequency proportional to a Doppler shift frequency produced by scanning the reflector; and (iii) a second filter coupled to the output from the photodetector having a passband centered at a multiple of the frequency.

DETAILED DESCRIPTION

Figure 1:
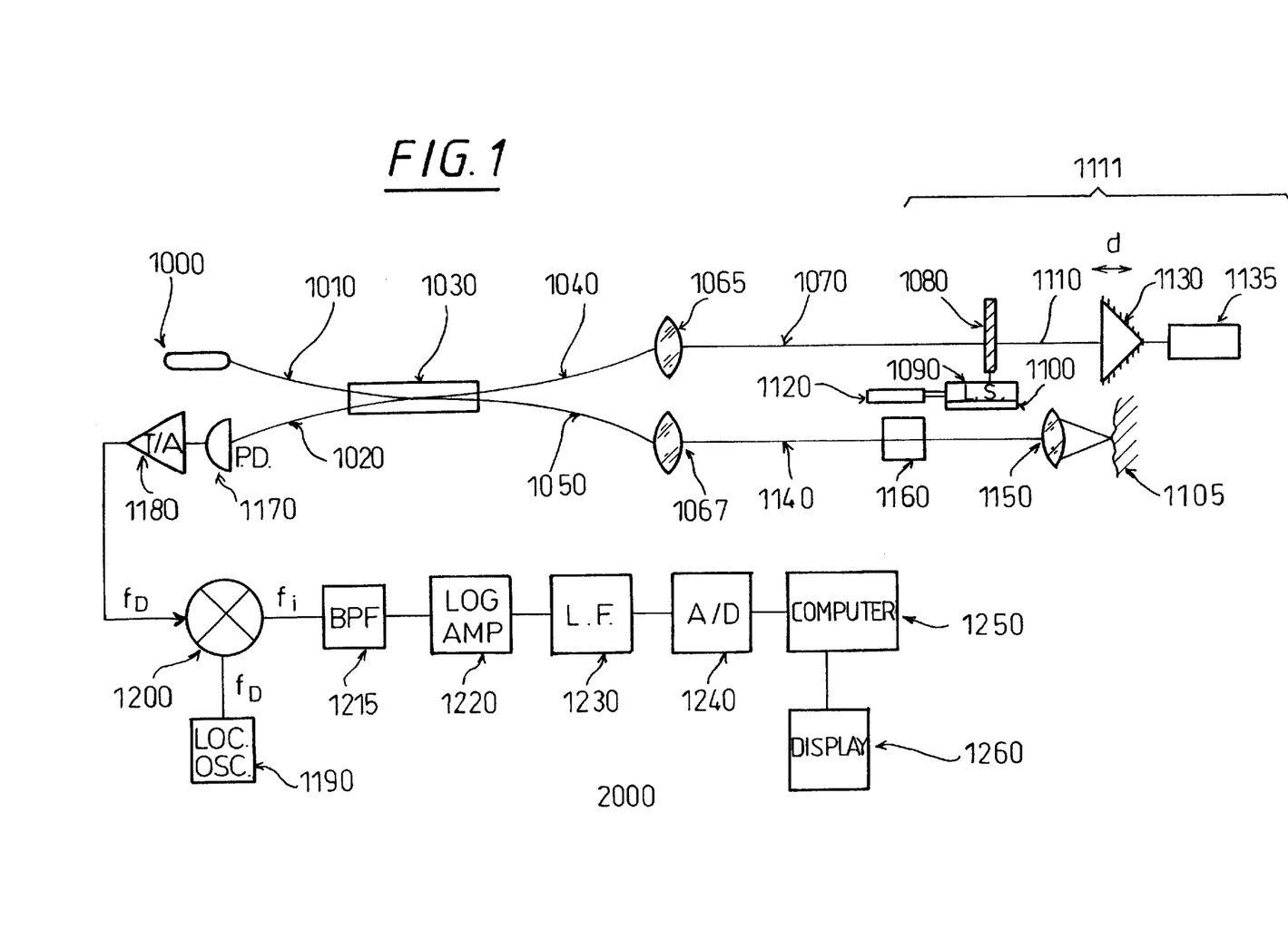
FIG. 1 shows, in pictorial form, an embodiment of an OCT apparatus which is fabricated in accordance with the present invention.

FIG. 1 shows, in pictorial form, embodiment 2000 of the present invention that is used to investigate sample objects. As shown in FIG. 1, embodiment 2000 of the present invention is comprised of a low coherence radiation source 1000. Low coherence radiation source 1000 may be embodied in a number of ways which are well known to those of ordinary skill in the art. In a preferred embodiment of the present invention, short coherence radiation source 1000 is a superluminescent diode (SLD). Radiation output from low coherence radiation source 1000 is applied over optical fiber 1010 as input to 3 dB radiation coupler 1030. 3 dB radiation coupler 1030 couples 50% of the radiation input thereto from low coherence radiation source 1000 into optical fibers 1040 and 1050, respectively. 3 dB radiation coupler 1030 may be embodied in a number of ways which are well known to those of ordinary skill in the art. In a preferred embodiment of the present invention, 3 dB radiation coupler 1030 is an optical fiber radiation coupler. Radiation output from optical fibers 1040 and 1050 is collimated by collimating lens systems 1065 and 1067, respectively, into reference arm path 1070 and sample arm path 1140 of embodiment 2000, respectively.

As further shown in FIG. 1, radiation in reference arm path 1070 impinges upon measurement range variation apparatus 1111. In particular, radiation in reference arm path 1070 impinges upon, and propagates through, 50% transmitter 1080 (for example, a 50% mirror). As shown in FIG. 1, 50% transmitter 1080 is mounted on linear stage translation apparatus 1090 and encoder 1100 provides a precise determination of the position of linear stage translation apparatus 1090. Linear stage translation apparatus 1090 and encoder 1100 may be embodied in a number of ways which are well known to those of ordinary skill in the art. As shown in FIG. 1, encoder 1100 is affixed to linear stage translation apparatus 1090. In accordance with the present invention, linear stage translation apparatus 1090 is driven by motor 1120 so that distance 1110 between 50% transmitter 1080 and retroreflector 1130 can be adjusted. In addition, retroreflector 1130 is translated at constant speed V back and forth through a distance d, which distance d will be referred to below as a scan range d. The translation of retroreflector 1130 may be accomplished in a number of ways which are well known to those of ordinary skill in the art. In a preferred embodiment of the present invention, high speed galvanometer 1135 is affixed to retroreflector 1130 to provide the desired translation.

Radiation in sample arm path 1140 impinges upon and propagates through transverse scanning apparatus 1160. Radiation output from transverse scanning apparatus 1160 is focused by focusing lens system 1150 onto sample 1105. As is well known to those of ordinary skill in the art, transverse scanning apparatus 1160 provides a two dimensional transverse scan of radiation in sample arm path 1140 over sample 1105. Further, transverse scanning apparatus 1160 may be embodied in a number of ways which are well known to those of ordinary skill in the art.

Radiation transmitted back into reference arm path 1070 through 50% transmitter 1080 and radiation transmitted back into sample arm path 1140 through transverse scanning apparatus 1160 is applied as input by collimating lens systems 1065 and 1067, respectively, into optical fibers 1040 and 1050, respectively. Radiation output from optical fibers 1040 and 1050 is applied as input to 3 dB radiation coupler 1030. 3 dB radiation coupler 1030, in turn, combines radiation coupled thereinto from reference arm path 1070 and sample arm path 1140 and couples the combined radiation into optical fiber 1020. It should be understood that although the present invention has been described in the context of an embodiment which utilizes optical fibers, the present invention is not limited thereto and further embodiments may be readily fabricated by those of ordinary skill in the art using discrete optical components as well as integrated optics.

Radiation output from optical fiber 1020 is applied as input to photodetector 1170. As is well known to those of ordinary skill in the art, when the mismatch between the optical pathlength between radiation combined in 3 dB radiation coupler 1030 from reference arm path 1070 and sample arm path 1140 is less than the coherence length of radiation source 1000, a measurably useful interference signal is output from photodetector 1170. In accordance with embodiment 2000 of the present invention, the interference signal output from photodetector 1170 is applied as input to transimpedance amplifier 1180. Output from transimpedance amplifier 1180 is applied as input to mixer 1200 along with a signal generated by tunable local oscillator 1190. Photodetect 1170, transimpedance amplifier 1180, tunable local oscillator 1190, and mixer 1200 may be embodied in a number of ways which are well known to those of ordinary skill in the art.

As is well known to those of ordinary skill in the art, since retroreflector 1130 is scanned back and forth at a constant speed V, the interference signal output from photodetector, and hence the signal applied as input to mixer 1200 from transimpedance amplifier 1180 is modulated with a Doppler shift frequency $f_D$ where:

$$f_D = 2V/\lambda \tag{1}$$

$$V = d/t \tag{2}$$

where: (i) $\lambda$=wavelength of the radiation output from low coherence radiation source 1000; (ii) V is the effective velocity of the scan; (iii) d is the scan range of retroreflector 1130; and (iv) t is the scan time.

As is well known to those of ordinary skill in the art, mixer 1200, together with local oscillator 1190, functions like a frequency converter widely used in AM/FM receivers to generate a signal having an intermediate frequency $f_i$, where $f_i = f_o - f_D$ ($f_o$ is the frequency of local oscillator 1190). It is well known that mixer 1200 also produces a number of frequencies, for example, $f_o + f_D$. Although the higher frequency produces a better signal-to-noise ratio, amplifier bandwidths are more limited at higher frequencies.

In accordance with embodiment 2000 of the present invention, the signal output from mixer 1200 is applied as input to bandpass filter 1215, the passband of bandpass filter 1215 being centered at $f_i$. The signal output from bandpass filter 1215 is applied as input to log amplifier 1220 which serves both as a rectifier and as a logarithmic amplifier to convert the signal envelop of the input signal to a logarithm scale signal. The bandwidth of the signal at the intermediate frequency $f_i$ is proportional to the spectral bandwidth of the signal output from low coherence radiation source 1000 ($\Delta f_i = 2\pi c \Delta \lambda / \lambda^2$, where c equals the speed of light). The bandwidth of bandpass filter 1215 is selected to be broad enough to allow substantially all of the signal components to pass through, yet the bandwidth is selected to be as narrow as possible to eliminate most of the noise.

The signal output from log amplifier 1220 is applied as input to lowpass filter 1230 and output from lowpass filter 1230, in turn, is applied as input to A/D converter 1240. A/D converter 1240 converts the input signal to a digital signal and the digital signal output from A/D converter 1240 is applied as input to computer 1250. Computer 1250 processes the raw signal, for example, to measure the eye length and to display the processed results on display monitor 1260, for example, using a color map. Bandpass filter 1215, log amplifier 1220, lowpass filter 1230, A/D converter 1240, computer 1250, and display monitor 1260 may be embodied in a number of ways which are well known to those of ordinary skill in the art.

Figure 2:
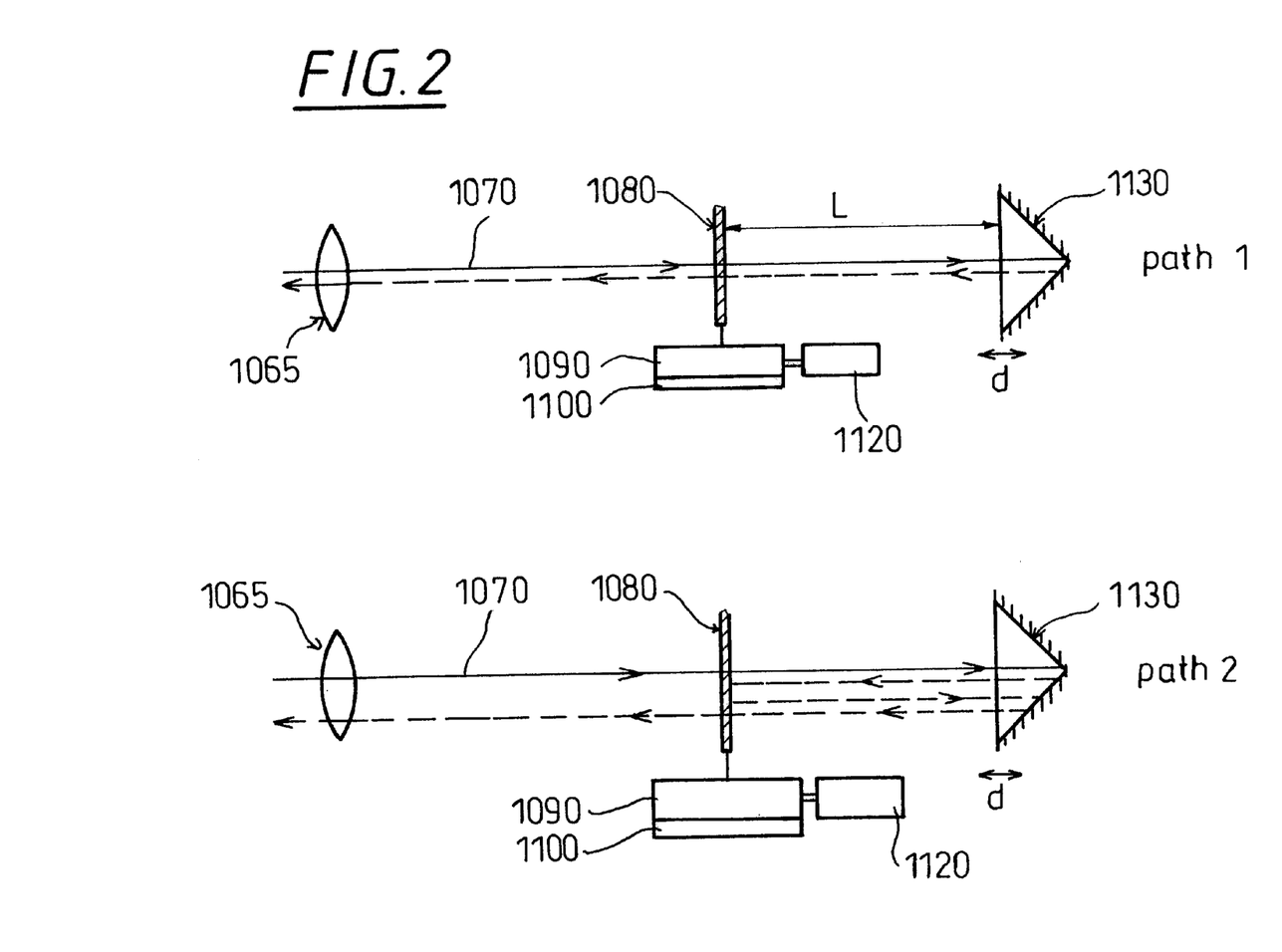
FIG. 2 shows, in pictorial form, shows two of many possible paths for radiation traversing a reference arm path of the embodiment of the present invention shown in FIG. 1.

FIG. 2 shows, in pictorial form, two of many possible optical paths for radiation traversing reference arm path 1070 of embodiment 2000 of the present invention showm in FIG. 1. For path 1 of FIG. 2, the maximum and minimum of optical pathlength traversed between 50% transmitter 1080 and retroreflector 1130 is equal to 2(L±d/2), respectively (where L is the distance between 50% transmitter 1080 and the midpoint of translation of retroreflector 1130 and d is the total distance retroreflector 1130 is translated, i.e., the scan range of retroreflector 1130). For path 1, the Doppler frequency of the interference signal output from photodetector 1170 $f_{D1}=f_D$ (where $f_D$ is the value provided by eqn. (1) above). For path 2 of FIG. 2, radiation bounces back and forth between 50% transmitter 1080 and retroreflector 1130 twice before passing through 50% transmitter 1080 back to collimating lens system 1065. Thus, for path 2, the maximum and minimum of optical pathlength traversed between 50% transmitter 1080 and retroreflector 1130 is equal to 4(L±d/2), respectively. Using eqn. (2) above, the effective velocity of the scan of retroreflector 1130 is equal to 2 V. As a result, for path 2, the Doppler frequency of the interference signal output from photodetector 1170 $f_{D2}=2f_D$.

As one can readily appreciate, if bandpass filter 1215 is centered at $f_i = f_o - f_D$ to pass a signal generated by path 1, the intermediate frequency $f_{i2}(=f_o - 2f_D)$ of the signal output from mixer 1200 for path 2 will not pass through bandpass filter 1215. In this case, therefore, as should be readily understood by those of ordinary skill in the art, a longitudinal scan into sample 1105 with depth d can be observed. However, if the frequency of tunable local oscillator 1190 is tuned at $f_{O2}(=f_o + f_D)$, the intermediate frequency $f_{i2}(=f_o + f_D - 2f_D = f_o - f_D = f_i)$ will pass through bandpass filter 1215 and a longitudinal scan into sample 1105 with depth 2d can be observed.

Generalizing from the above, and in accordance with the present invention, for the embodiment of the present invention shown in FIG. 1, if the frequency of tunable local oscillator 1190 is tuned at $f_{ON}(=f_o + (N-1)f_D)$, the intermediate frequency $f_{iN}(=f_o + (N-1)f_D - Nf_D = f_o - f_D = f_i)$ will pass through bandpass filter 1215 and a longitudinal scan into sample 1105 with depth Nd can be observed.

However, since the intensity of radiation coupled back to 3 dB radiation coupler from reference arm path 1070 will be reduced by $0.5(0.5R)^N$, where R is the reflectance of retroreflector 1130, the potential scan depth range may be limited by the number of bounces between 50% transmitter 1080 and retroreflector 1130. The reflectance of a solid glass retroreflector which is based on total internal reflection and which has an anti-reflection coating on the face side can have a value of R higher than 0.9. An additional concern is that for a shot noise limited system, radiation output from reference arm path 1070 signal is preferably kept larger than radiation output from sample arm path 1140. In particular, for ophthalmic applications of embodiments of the present invention, since the reflectance of an eye is less than $10^{-4}$ of the incident radiation intensity, N can be as large as 4 to 5.

Figure 3:
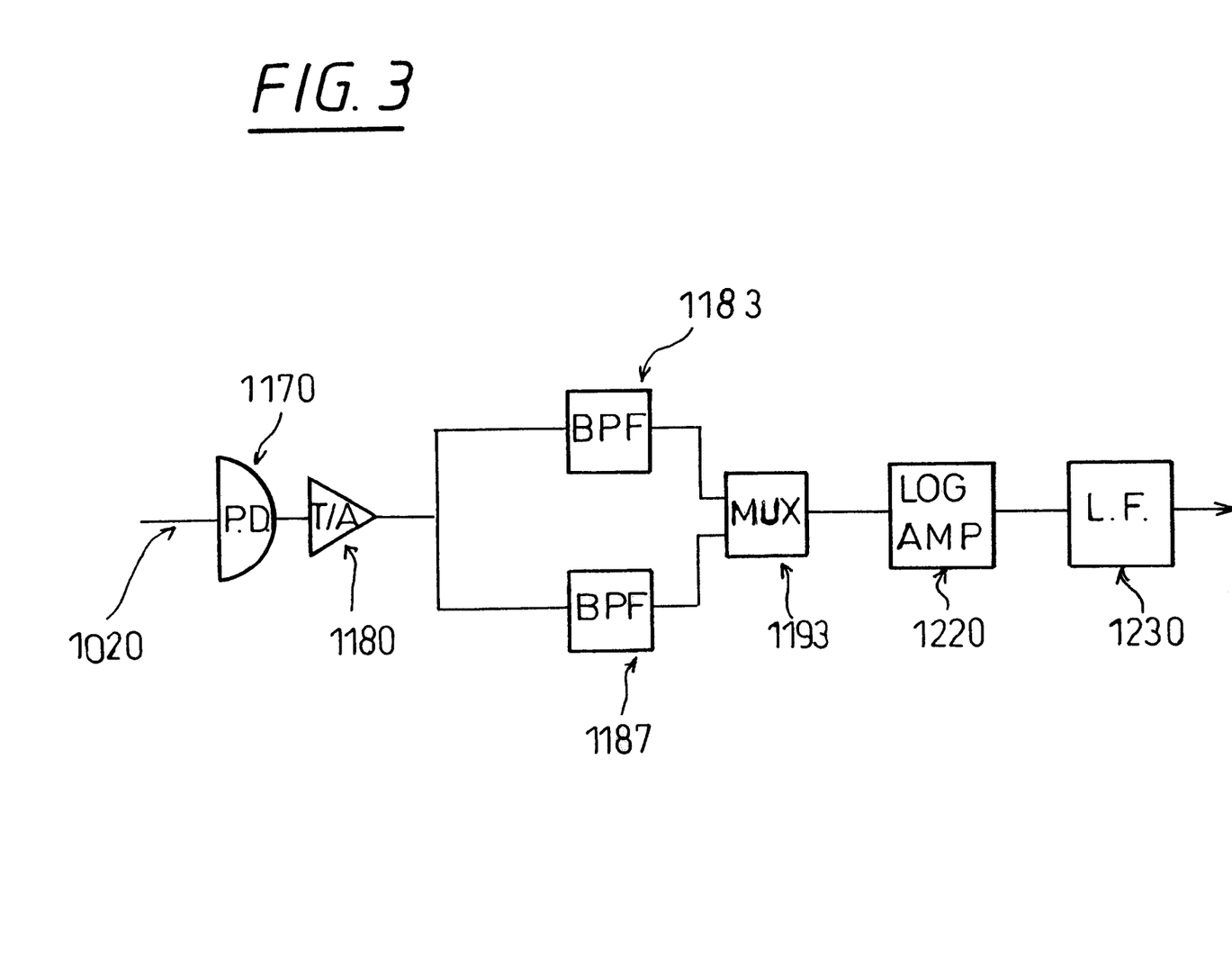
FIG. 3 is a diagram of a signal analysis section of an OCT apparatus which is fabricated in accordance with the present invention, which OCT apparatus is adapted to measuring the length of an eye.

FIG. 3 is a diagram of a signal analysis section of an OCT apparatus which is fabricated in accordance with the present invention, which OCT apparatus is adapted to measuring the length of an eye. The signal analysis section shown in FIG. 3 replaces the signal analysis section shown in FIG. 1 which is comprised of circuit elements between transimpedance amplifier 1180 and A/D 1240. For the following, assume that two signals have been received by photodetector 1170, one of the two signals corresponds to path 1 of FIG. 2 and the second of the two signals corresponds to path 2 of FIG. 2.

As shown in FIG. 3, the two signals are applied as input to photodetector 1170. The output from photodetector 1170 is applied as input to transimpedance amplifier 1180, and the output from transimpedance amplifier 1180 is applied, in turn, as input to bandpass filters 1183 and 1187. Bandpass filters 1183 and 1187 have their passband frequencies centered at $f_1(=f_D)$ and $f_2(=2f_D)$, respectively. As shown in FIG. 3, bandpass filters 1183 and 1187 are connected in parallel between transimpedance amplifier 1180 and multiplexer 1193.

Figure 4:
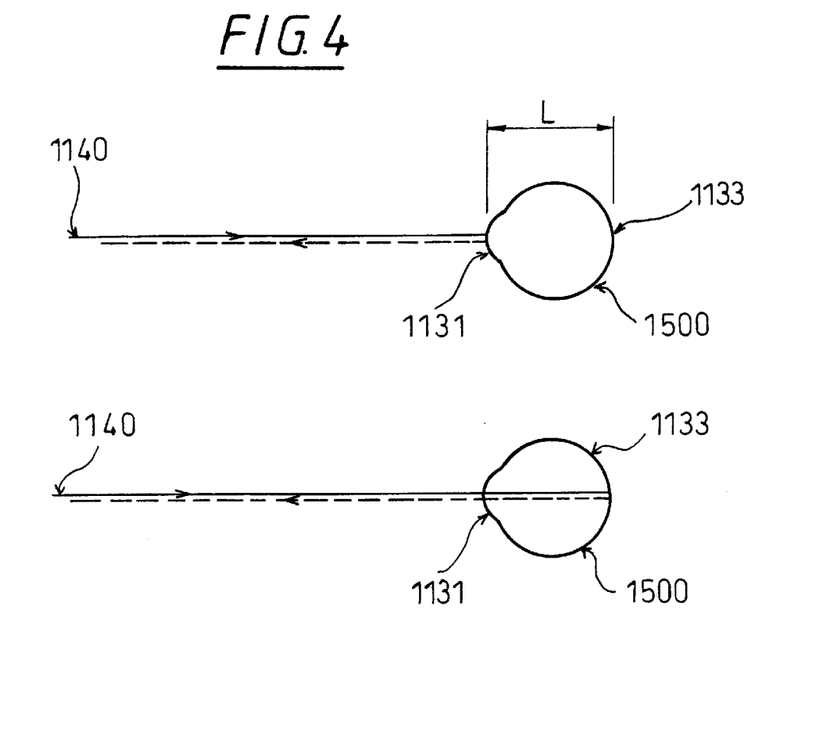
FIG. 4 shows, in pictorial form, how an embodiment of the present invention which combines the embodiments of FIGS. 1 and 3 utilizes reflections from an eye to generate two radiation signals in the sample arm path which interfere with two radiation signals generated in the reference arm path (referring to FIG. 2), wherein interference between these two sets of radiation signals can be observed at the same time to measure the eye length.

FIG. 4 shows, in pictorial form, how an embodiment of the present invention which combines the embodiments of FIGS. 1 and 3 utilizes reflections from an eye to generate two radiation signals in sample arm path 1140 which interfere with two radiation signals generated in reference arm path 1070, wherein interference between these two sets of radiation signals can be observed at the same time to measure the eye length. To do this, one selects the distance L between 50% transmitter and retroreflector 1130 equal to the eye length of an average human eye. Now, referring to FIG. 4, the first signal generated in sample arm path 1140 results from reflection of radiation from cornea 1131 of eye 1500 and the second signal generated in sample arm path 1140 results from reflection of radiation from retina 1133 of eye 1500. Then, as one can readily appreciate, the first interference signal is generated by interference between radiation in reference arm path 1070 arising from path 1 shown in FIG. 2 and radiation in sample arm path 1140 arising from reflection from cornea 1131 shown in FIG. 4. Similarly, the second interference signal is generated by interference between radiation in reference arm path 1070 arising from path 2 shown in FIG. 2 and radiation in sample arm path 1140 arising from reflection from retina 1133 shown in FIG. 4.

Figure 5:
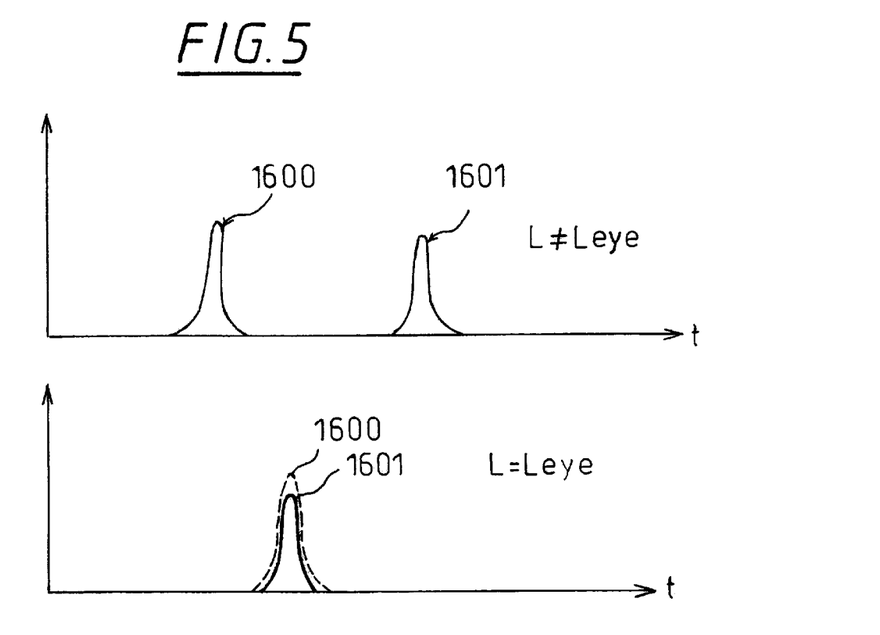
FIG. 5 shows, in graphical form, two interference signals generated in accordance with the present invention to measure the length of an eye.

FIG. 5 shows, in graphical form, the two interference signals obtained and displayed on display 1260. As shown in FIG. 5, by signals 1600 and 1601, if L (the length of an average human eye) is not equal to $L_{eye}$ (the length of a patient's eye), and the difference between L and $L_{eye}$ is less than the scan range d, then both interference signals will be observed with a time delay. In accordance with the present invention, the length of the eye can be measured by causing motor 1090 to move 50% transmitter 1080, for example, by interaction with computer 1250, so that signals 1600 and 1601 coincide in time as shown in FIG. 5. As can be readily appreciated, this movement may be caused by input from an operator using inputs derived from a number of devices (not shown) which are well known to those of ordinary skill in the art such as a joy stick, a mouse and the like. Alternatively, computer 1250 may be programmed to overlap the two signals using methods which are well known to those of ordinary skill in the art. The position of 50% transmitter 1080 is relayed to computer 1250 from encoder 1100 and computer 1250 uses the position to make the measurement. Advantageously, in accordance with the present invention, the accuracy of the measurement is the coherence length of the low coherence radiation source 1000.

Figure 6:
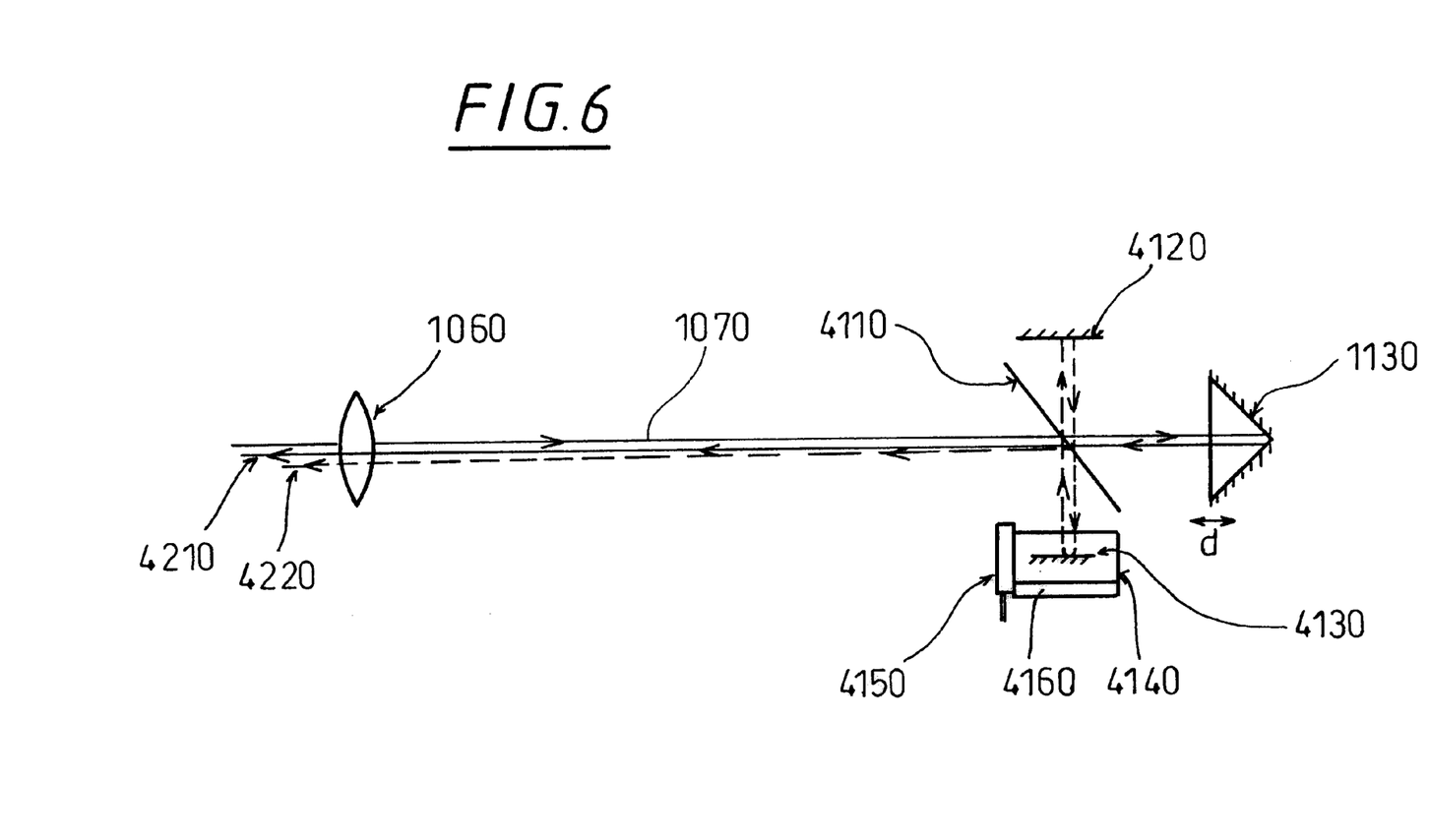
FIG. 6 shows, in pictorial form, an alternative embodiment of the reference arm of the OCT apparatus shown in FIG. 1.

FIG. 6 shows, in pictorial form, an alternative embodiment of a reference arm for use in embodiment 2000 shown in FIG. 1. As shown in FIG. 6, 50/50 beamsplitter 4110 splits the incoming radiation in reference arm path 1070 so that it travels over two optical paths. In the first optical path: (a) radiation passes through beamsplitter 4110; (b) is reflected from retroreflector 1130; (c) passes through beamsplitter 4110 again; and (d) passes through collimating lens 1060 as radiation 4210. In this embodiment, retroreflector 1130 is scanned with a velocity V, so that the Doppler shift frequency is $f_D$ for the first optical path. For this embodiment, the optical pathlength for the first optical path is initially set equal to the optical pathlength of radiation reflected from the cornea of an eye that emerges from sample arm path 1140. In the second optical path: (a) radiation passes through beamsplitter 4110; (b) is reflected from retroreflector 1130; (c) is reflected from beamsplitter 4110 to mirror 4120; (d) is reflected from mirror 4120; (e) passes through beamsplitter 4110; (f) is reflected from mirror 4130 which is mounted on linear stage 4140; (g) is reflected from beamsplitter 4110; and (h) passes through collimating lens 1060 as radiation 4220. It should be understood that mirrors 4120 and 4130 can also be retroreflectors like retroreflector 1130. Since the radiation which traverses the second optical path is only reflected from retroreflector 1130 once, the Doppler frequency shift is $f_D$ for the second optical path. Then, in accordance with the present invention, the optical distance between mirrors 4120 and 4130 is set to the optical pathlength of an average human eye. As a result, the total optical pathlength traversed by radiation 4220 is equal to the optical pathlength length traversed by the sample beam reflected from the retina. Further, in accordance with the present invention, motor 4150 moves linear stage translation apparatus 4140 in response to signals sent thereto from computer 1250 so that the location of the interference signal generated by radiation reflected from the cornea and the location of the interference signal generated by radiation reflected from the retina coincide in the manner described above. The position of mirror 4130 is relayed to computer 1250 by encoder 4160. In this manner, the eye length information is obtained from the optical pathlength between mirrors 4120 and 4130. A calibration procedure can precisely determine the length measurement. An advantage of this alternative embodiment is that only a single channel bandpass filter in the detector electronics is required since the same Doppler frequency is generated for each of the reference arm signals 4210 and 4220.

Lastly, although the present invention has been described in terms of measurement of the length of a human eye, the present invention is not so limited. In fact, as can readily be appreciated by those of ordinary skill in the art, embodiments of the present invention can be used to measure the distance between two parts of an object. Further, embodiments of the present invention may be fabricated utilizing discrete optical components, integrated optics, optical fibers and combinations of the same. Still further, other embodiments may utilize couplers and transmitters that differ from the 50% coupler and 50% transmitters described above and, in light of the descriptions above, it should be clear to those of ordinary skill in the art how the above-described embodiments may be altered to account for such differences.

Those skilled in the art will recognize that the foregoing description has been presented for the sake of illustration and description only. As such, it is not intended to be exhaustive or to limit the invention to the precise form disclosed.

What is claimed is:

1. An optical coherence tomography apparatus ("OCT") which examines an object, which OCT apparatus comprises:

a source of short coherence radiation;

a coupler which: (a) couples a first portion of the radiation to a reference arm; (b) couples a second portion of the radiation to a sample arm; (c) combines radiation transmitted thereto from the reference arm and the sample arm; and (d) couples the combined radiation to an analyzer;

wherein:
the reference arm transmits the first portion of the radiation to a measurement range variation apparatus and transmits radiation output from the measurement range variation apparatus back to the coupler;
the sample arm transmits the second portion of the radiation to the object and transmits radiation scattered by the object back to the coupler; and
the measurement range variation apparatus comprises:
a transmitter which transmits a portion of the radiation incident thereupon;

a reflector which reflects radiation transmitted by the transmitter, which transmitter reflects a portion of the reflected radiation; and a scanner coupled to scan the reflector.

2. The OCT apparatus of claim 1 wherein the analyzer comprises:

a photodetector which detects radiation coupled from the coupler;

a mixer responsive to output from the photodetector and an oscillator; and a filter coupled to the output from the mixer.

3. The OCT apparatus of claim 2 wherein the oscillator is a tunable oscillator.

4. The OCT apparatus of claim 2 wherein the filter has a passband frequency centered substantially at a frequency output from the mixer determined from a frequency of the oscillator and a frequency proportional to a Doppler shift frequency produced by scanning the reflector in the output from the photodetector.

5. The OCT apparatus of claim 4 wherein the frequency of the oscillator comprises a first frequency plus a frequency proportional to the Doppler shift frequency.

6. The OCT apparatus of claim 4 wherein passband frequency is centered at the difference between the frequency of the oscillator and the Doppler shift frequency.

7. The OCT apparatus of claim 1 wherein the reflector is a retroreflector.

8. The OCT apparatus of claim 1 which measures a distance between a first and a second scattering portion in the object wherein:

the measurement range variation apparatus further comprises a translator coupled to translate the transmitter; and the analyzer comprises:

a photodetector which detects radiation coupled from the coupler;

a first filter coupled to output from the photodetector and having a passband centered substantially at a frequency proportional to a Doppler shift frequency produced by scanning the reflector; and a second filter coupled to the output from the photodetector having a passband centered substantially at a multiple of the frequency.

9. The OCT apparatus of claim 8 wherein the analyzer further comprises a display which displays a signal generated as a result of radiation scattered from the first scattering portion and a signal generated as a result of radiation scattered from the second scattering portion.

10. The OCT apparatus of claim 9 wherein the measurement range variation apparatus further comprises an encoder which measures the position of the transmitter.

11. The OCT apparatus of claim 10 wherein the analyzer further comprises a computer which sends a signal to the translator to cause the two signals to coincide and receives a signal from the encoder to provide thereby a measurement of the distance.

12. The OCT apparatus of claim 8 wherein:

the measurement range variation apparatus further comprises an encoder which measures the position of the transmitter; and the analyzer further comprises a computer which sends a signal to the translator to cause a first signal output from the first filter and a second signal output from the second filter to overlap, and receives a signal from the encoder to determine the measurement of the distance.

13. The OCT apparatus of claim 1 which measures a distance between a first and a second scattering portion in the object wherein:

the measurement range variation apparatus further comprises a translator coupled to translate the third reflector; and the analyzer comprises:

a photodetector which detects radiation coupled from the coupler; and a filter coupled to output from the photodetector and having a passband centered substantially at a frequency proportional to a Doppler shift frequency produced by scanning the first reflector.

14. The OCT apparatus of claim 13 wherein the analyzer further comprises a display which displays a signal generated as a result of radiation scattered from the first scattering portion and a signal generated as a result of radiation scattered from the second scattering portion.

15. The OCT apparatus of claim 14 wherein the measurement range variation apparatus further comprises an encoder which measures the position of the third reflector.

16. The OCT apparatus of claim 15 wherein the analyzer further comprises a computer which sends a signal to the translator to cause the two signals to coincide and receives a signal from the encoder to provide thereby a measurement of the distance.

17. The OCT apparatus of claim 13 wherein:

the measurement range variation apparatus further comprises an encoder which measures the position of the third reflector; and the analyzer further comprises a computer which sends a signal to the translator to cause a first signal generated as a result of radiation scattered from the first scattering portion and a second signal generated as a result of radiation scattered from the second scattering portion to overlap, and receives a signal from the encoder to determine the measurement of the distance.

18. An optical coherence tomography apparatus ("OCT") which examines an object, which OCT apparatus comprises:

a source of short coherence radiation;

a coupler which: (a) couples a first portion of the radiation to a reference arm; (b) couples a second portion of the radiation to a sample arm; (c) combines radiation transmitted thereto from the reference arm and the sample arm; and (d) couples the combined radiation to an analyzer;

wherein:

the reference arm transmits the first portion of the radiation to a measurement range variation apparatus and transmits radiation output from the measurement range variation apparatus back to the coupler;

the sample arm transmits the second portion of the radiation to the object and transmits radiation scattered by the object back to the coupler; and the measurement range variation apparatus comprises:

a beamsplitter which transmits a portion of the radiation incident thereupon in a direction from the reference arm to a first reflector;

second and third reflectors disposed to reflect radiation incident thereupon along a second direction; and a scanner coupled to scan the first reflector.

19. The OCT apparatus of claim 18 wherein the first reflector is a retroreflector.

20. A measurement range variation apparatus for use in a reference arm of an optical coherence tomography apparatus comprises:

a transmitter which transmits a portion of radiation incident thereupon;

a translator coupled to translate the transmitter;

a reflector which reflects radiation transmitted by the transmitter, which transmitter reflects a portion of the reflected radiation;

a scanner coupled to scan the reflector; and an encoder which measures the position of the transmitter.

21. A measurement range variation apparatus for use in a reference arm of an optical coherence tomography apparatus comprises:

a beamsplitter which transmits a portion of radiation incident thereupon in a direction to a first reflector;

second and third reflectors disposed to reflect radiation incident thereupon along a second direction;

a scanner coupled to scan the first reflector;

a translator coupled to translate the third reflector; and an encoder which measures the position of the third reflector.

22. A method for examining an object which comprises the steps of:

generating short coherence radiation;

coupling a first portion of the radiation into a reference arm and a second portion of the radiation into a sample arm;

in the reference arm, transmitting the first portion of the radiation to a measurement range variation apparatus which comprises a transmitter which transmits a portion of the radiation incident thereupon; a reflector which reflects radiation transmitted by the transmitter, which transmitter reflects a portion of the reflected radiation; and a scanner coupled to scan the reflector;

in the sample arm, transmitting the second portion of the radiation to the object;

combining radiation scattered by the object with radiation obtained from the measurement range variation apparatus; and analyzing the combined radiation.

23. The method of claim 22 which measures a distance between a first and a second scattering portion in the object wherein:

the measurement range variation apparatus further comprises a translator coupled to translate the transmitter; and the step of analyzing comprises:
generating a signal by detecting the combined radiation;
filtering the signal using a first filter having a passband centered substantially at a frequency proportional to a Doppler shift frequency produced by scanning the reflector; and
filtering the signal using a second filter having a passband centered substantially at a multiple of the frequency.

24. The method of claim 23 wherein:

the measurement range variation apparatus further comprises an encoder which measures the position of the transmitter; and the step of analyzing further comprises:
sending a signal to the translator to cause a first signal output from the first filter and a second signal output from the second filter to overlap, and
receiving a signal from the encoder to determine the measurement of the distance.

25. A method for examining an object which comprises the steps of:

generating short coherence radiation;

coupling a first portion of the radiation into a reference arm and a second portion of the radiation into a sample arm;

in the reference arm, transmitting the first portion of the radiation to a measurement range variation apparatus which comprises a beamsplitter which transmits a portion of the radiation incident thereupon in a direction from the reference arm to a first reflector; second and third reflectors disposed to reflect radiation incident thereupon along a second direction; and a scanner coupled to scan the first reflector;

in the sample arm, transmitting the second portion of the radiation to the object;

combining radiation scattered by the object with radiation obtained from the measurement range variation apparatus; and analyzing the combined radiation.

26. The method of claim 25 which measures a distance between a first and a second scattering portion in the object wherein:

the measurement range variation apparatus further comprises a translator coupled to translate the third reflector; and the step of analyzing comprises:
generating a signal by detecting the combined radiation; and
filtering the signal using a filter having a passband centered substantially at a frequency proportional to a Doppler shift frequency produced by scanning the first reflector.

27. The method of claim 26 wherein:

the measurement range variation apparatus further comprises an encoder which measures the position of the third reflector; and the step of analyzing further comprises:
sending a signal to the translator to cause a first signal generated as a result of radiation scattered from the first scattering portion and a second signal generated as a result of radiation scattered from the second scattering portion to overlap; and
receiving a signal from the encoder to determine the measurement of the distance.

* * * * *